US009259147B2

(12) United States Patent
Baranton et al.

(10) Patent No.: US 9,259,147 B2
(45) Date of Patent: Feb. 16, 2016

(54) BINOCULAR MULTIPLEXING METHOD AND DEVICE

(71) Applicants: Konogan Baranton, Charenton Le Pont (FR); Guilhem Escalier, Charenton Le Pont (FR); Benjamin Rousseau, Charenton Le Pont (FR)

(72) Inventors: Konogan Baranton, Charenton Le Pont (FR); Guilhem Escalier, Charenton Le Pont (FR); Benjamin Rousseau, Charenton Le Pont (FR)

(73) Assignee: ESSILOR INTERNATIONAL (COMPAGNIE GENERALE D'OPTIQUE), Charenton Le Pont (FR)

( * ) Notice: Subject to any disclaimer, the term of this patent is extended or adjusted under 35 U.S.C. 154(b) by 81 days.

(21) Appl. No.: 14/366,181

(22) PCT Filed: Dec. 14, 2012

(86) PCT No.: PCT/FR2012/052946
§ 371 (c)(1),
(2) Date: Jun. 17, 2014

(87) PCT Pub. No.: WO2013/093308
PCT Pub. Date: Jun. 27, 2013

(65) Prior Publication Data
US 2014/0362345 A1    Dec. 11, 2014

(30) Foreign Application Priority Data

Dec. 22, 2011 (FR) ..................................... 11 04037

(51) Int. Cl.
*A61B 3/10* (2006.01)
*A61B 3/00* (2006.01)
(Continued)

(52) U.S. Cl.
CPC .................. *A61B 3/10* (2013.01); *A61B 3/0008* (2013.01);
(Continued)

(58) Field of Classification Search
USPC ........................................... 351/211, 212, 246
See application file for complete search history.

(56) References Cited

U.S. PATENT DOCUMENTS

| 5,777,718 | A | 7/1998 | Kohayakawa |
| 5,872,614 | A | 2/1999 | Ueno |
| 6,309,068 | B1 | 10/2001 | Kohayakawa |

FOREIGN PATENT DOCUMENTS

JP        7088081 A    4/1995

OTHER PUBLICATIONS

International Search Report, dated Mar. 4, 2013, from corresponding PCT application.

*Primary Examiner* — Jack Dinh
(74) *Attorney, Agent, or Firm* — Young & Thompson (57) ABSTRACT

A binocular multiplexing device for a single-channel ophthalmological instrument for objective measurement of at least one vision parameter of a subject, the ophthalmological instrument including elements for generating a single light beam, elements for collecting a measurement beam by reflecting and/or refracting the light beam against the subject's eye and a sensor associated with the single measurement channel. The binocular multiplexing device includes optical separation first elements for receiving an image beam originating from a stimulus target and separating the image beam into a right and left ocular stimulation beam; optical switching elements for switching the single light beam selectively onto a right or left monocular light beam's optical path to form, after reflection and/or refraction by the eye in question, a right, respectively left, ocular measurement beam, and optical combination elements for superimposing the right, respectively left, ocular stimulation beam, and the right, respectively left, monocular light beam.

21 Claims, 6 Drawing Sheets

(51) Int. Cl.
*A61B 3/103* (2006.01)
*A61B 3/107* (2006.01)
*A61B 3/036* (2006.01)
*G02B 27/14* (2006.01)

(52) U.S. Cl.
CPC ............ *A61B 3/0025* (2013.01); *A61B 3/0091* (2013.01); *A61B 3/103* (2013.01); *A61B 3/107* (2013.01); *A61B 3/036* (2013.01); *G02B 27/141* (2013.01)

BINOCULAR MULTIPLEXING METHOD AND DEVICE

TECHNICAL FIELD OF THE INVENTION

Generally, the present invention relates to the field of binocular optometric methods, instruments and devices. More particularly the invention relates to an optometric apparatus based on the measurement of reflection and/or refraction of an illuminating beam from each eye. The aim of optometric measurements is to determine the values of a prescription for a pair of spectacle lenses for correcting vision. These binocular measurements are intended to be used for the optical design and the manufacture of the refracting faces of spectacle lenses for correcting far vision and near vision (including reading glasses and non-prescription glasses), whether it is a question of passive lenses or lenses having electronically controlled variable optical powers.

PRIOR ART

Most commercially available optometric instruments are monocular. A first type of monocular apparatus is based on a monocular device comprising a stimulus and a monocular measuring system. The monocular device is placed in front of an eye in order to carry out a first measurement, then moved in front of the other eye in order to carry out a second measurement. The drawback of double monocular measurements is that they are carried out under conditions that do not replicate the natural vision of the subject, which is binocular. With near vision in particular, prismatic convergence changes the sight axis of the eyes. Physiological constraints such as the application of muscular effort may cause the refraction of the eyes or the pressure of the eyelids on the cornea to change. Depending on the subject, a near-vision measurement along the sight axis of a binocular stimulus may be different from a monocular vision measurement along a sight axis oriented straight in front of the subject. In addition, in a monocular system, the stimulus and the measuring system must be moved to change eyes. Thus, the subject sees the stimulus with the first measured eye, then during the changeover the two eyes are no longer stimulated until the apparatus arrives in front of the other eye. This movement subjects the eyes of the subject to a light intensity variation, temporarily freeing the subject from the stimulus and possibly causing a pupillary dilation or contraction, such as if the subject blinks. Points of reference and the frame of reference may shift in the time lapse between the two monocular measurements, thus corrupting the measurements.

Solutions in which the stimulus is binocular and the measurement monocular do exist. The monocular measuring system of these solutions must be moved mechanically between each eye. Although the change in the alignment of the monocular measuring system cannot be seen by the subject, the noise or vibrations generated by the movement may distract her/him from the stimulus, modifying their accommodation, and the size and/or position of her/his pupil. In addition, the binocular measurement of these solutions remains based on two sequential monocular measurements. However, the shorter the time lapse between two monocular measurements, the smaller the difference in accommodation between the two eyes, thereby limiting measuring errors induced by fluctuations in accommodation.

Binocular measuring instruments that comprise two monocular measuring apparatuses aligned with each of the two eyes, respectively, also exist, each monocular measuring apparatus comprising its own stimulus. In these binocular optometric instruments, the two stimuli are generally based on the same visual objects or the same pattern, but the two stimuli are physically different. Thus, the two stimuli will not be perfectly identical for both eyes, in terms of inclination or orientation relative to each other for example. The drawback of such a solution is that it makes it difficult for the subject to fuse the two stimuli. Specifically, whether or not the subject is able to fuse the stimuli seen is largely dependent on the periphery of the stimulus, as well as its centre. People who have difficulty fusing two images are extremely sensitive to differences in their left/right vision.

In order to promote the fusion of the stimuli, it is therefore preferable to use only one physical stimulating element. Accommodation fluctuations are thus decreased, thereby facilitating binocular vision by people who have difficulty fusing two separate images.

Systems that incorporate a binocular system for viewing a common stimulus with a double measuring means for characterizing both eyes at the same time also exist. In this case, the measuring field of the measuring sensor receives signals originating from both eyes. This solution requires a measuring sensor that is larger, more complex and expensive than normal. In addition, this solution limits the dynamic range and resolution of the measurements. Furthermore, sensors with wide measuring fields are ad hoc components that are not fitted as standard in widely used apparatuses.

Thus, it is generally not possible to use the stimulus and measuring means of another apparatus (autorefractometer, aberrometer, etc.) to create binocular vision of the stimulus and to take the selected measurement.

SUBJECT OF THE INVENTION

It would be desirable to be able to carry out binocular ophthalmological measurements. In particular it would be desirable to be able to carry out measurements of refraction and/or reflection from both eyes simultaneously. Complementarily, it would also be desirable to be able to carry out binocular measurements of astigmatism or higher-order aberration.

One of the aims of the invention is to provide an optometric method and device for measuring a binocular ophthalmological parameter characterizing refraction and/or reflection from the eye of a subject, under preset binocular vision conditions.

The invention aims to provide an optometric device for measuring at least one binocular vision parameter in a natural gaze position of the subject.

In order to remedy the aforementioned drawbacks of the prior art, the present invention provides a binocular multiplexing device for an ophthalmological instrument having a single channel for objective measurement of at least one visual parameter of a subject, said ophthalmological instrument comprising means for generating a single illuminating beam, means for collecting a measuring beam generated by reflection and/or refraction of said illuminating beam from an eye of the subject, and a sensor associated with said single measuring channel.

According to the invention, the binocular multiplexing device comprises:

first optical splitting means able to receive a stimulating image beam issued from a stimulus test pattern and intended to stimulate accommodation by the subject, said first optical splitting means being able to split said stimulating image beam into a right ocular stimulating beam and a left ocular stimulating beam so as to stimulate accommodation by the right eye and left eye of the subject simultaneously;

second optical splitting means able to receive said single illuminating beam and to split said single illuminating beam into a right monocular illuminating beam and a left monocular illuminating beam, said right monocular illuminating beam and left monocular illuminating beam being intended to illuminate the right eye and the left eye of the subject, respectively, in order to form, after reflection and/or refraction from the eye in question, a right ocular measuring beam and a left ocular measuring beam, respectively;

optical switching means able to receive said right ocular measuring beam and said left ocular measuring beam and to steer in sequence said right ocular measuring beam and said left ocular measuring beam into said single measuring channel, respectively;

first optical combining means able to superpose the right ocular stimulating beam and the right monocular illuminating beam, and first optical means for directing the right ocular stimulating beam and the right monocular illuminating beam toward the right eye; and second optical combining means able to superpose the left ocular stimulating beam and the left monocular illuminating beam, and second optical means for directing the left ocular stimulating beam and the left monocular illuminating beam toward the left eye.

The following are other nonlimiting and advantageous features of the binocular multiplexing device according to the invention:

said first optical splitting means comprise a beam-splitting plate or a beam-splitting cube;

said optical switching means comprise a dichroic plate, an orientable mirror, a retractable mirror, an electro-optical modulator, an acousto-optical modulator and/or polarization-selecting means;

said second optical splitting means are merged with said optical switching means; and said second optical splitting means comprise a beam-splitting plate or a beam-splitting cube.

Advantageously, said first optical combining means comprise a dichroic plate able to superpose a right ocular stimulating beam in the visible domain and a right monocular illuminating beam in the infrared domain, and/or said second optical combining means comprise a dichroic plate able to superpose a left ocular stimulating beam in the visible domain and a left monocular illuminating beam in the infrared domain, respectively.

Also advantageously, the binocular multiplexing device furthermore comprises an optical port for coupling to an ophthalmological instrument having a single measuring channel, said optical coupling port being able to receive a stimulating image beam issued from a stimulus test pattern, and a single illuminating beam, and to transmit a single measuring beam, and mechanical and/or opto-mechanical means for aligning said ophthalmological instrument having a single measuring channel and said binocular multiplexing device, said mechanical and/or opto-mechanical aligning means comprising an alignment test pattern able to emit an optical aligning beam, and optical means able to superpose said aligning optical beam and said single measuring beam in the optical coupling port.

Advantageously, the binocular multiplexing device comprises a right exit pupil, a left exit pupil and imaging optical means, said right exit pupil being able to receive said right monocular illuminating beam and said right ocular measuring beam, and said left exit pupil being able to receive said left monocular illuminating beam and said left ocular measuring beam, respectively, and said imaging optical means being able to form the image of an exit pupil of said ophthalmological instrument having a single measuring channel on said right exit pupil and/or said left exit pupil.

Advantageously, the binocular multiplexing device comprises secondary illuminating means able to emit a secondary illuminating beam in the direction of the cornea of each eye, so as to generate a right ocular measuring beam and a left ocular measuring beam, respectively, in order to provide an analysis of the cornea by keratometry and/or corneal topography.

Advantageously, the binocular multiplexing device furthermore comprises an optical system placed on the optical path of the stimulating image beam, said optical system being able to correct an average sphere error of the two eyes.

Advantageously, the binocular multiplexing device furthermore comprises a first optical system placed on the optical path of the right ocular stimulating beam, and a second optical system placed on the optical path of the left ocular stimulating beam, said first optical system and said second optical system being able to correct a sphere and/or cylinder error of the right eye and of the left eye of the subject, respectively.

According to particular and advantageous aspects of the binocular multiplexing device according to the invention, the device comprises:

a right optical system placed between the first optical combining means and the right eye of the subject;

a left optical system placed between the second optical combining means and the left eye of the subject; and means for aligning said right optical system and said left optical system so as to adjust the pupillary distance depending on the prismatic convergence of the subject.

According to certain particular aspects:

the optical paths of the stimulating image beam, of the single illuminating beam and of the single measuring beam are coincident, and said binocular multiplexing device comprises third optical splitting means able to receive and to spatially split said stimulating image beam and said single illuminating beam, said third optical splitting means being able to receive said single measuring beam along an optical path that is the reverse of that of said single illuminating beam.

Advantageously, said third optical splitting means comprise a beam-splitting plate able to split a stimulating image beam in the visible domain and an illuminating beam in the infrared domain.

According to particular and advantageous aspects of the binocular multiplexing device according to the invention, the device comprises an electronic processing unit suitable for receiving a signal representative of the switching state of said optical switching means and to receive, in sequence, a first measurement representative of said right ocular measuring beam and a second measurement representative of said left ocular measuring beam, said electronic processing unit being able to combine said signal representative of the switching state and said first and second measurements in order to deliver a multiplexed binocular measurement of at least one vision parameter.

The invention also provides an ophthalmological instrument for multiplexed binocular measurement of at least one vision parameter of a subject, said ophthalmological instrument comprising a binocular multiplexing device according to one of the embodiments thereof, and ophthalmological means for measuring at least one vision parameter of a subject, said ophthalmological measuring means being able to generate a single illuminating beam and to receive and analyze a single measuring beam generated by reflection and/or refraction of said single illuminating beam from an eye of the subject, said single illuminating beam and said single measuring beam following reciprocal optical paths between said ophthalmological measuring means and the eye of the subject.

The invention also provides a method for determining at least one binocular vision parameter of a subject, said method comprising the following steps:

a) delivering a stimulating image beam for a proximity value P;
b) splitting the stimulating image beam into a right ocular stimulating beam and a left ocular stimulating beam, so as to stimulate accommodation by the right eye and by the left eye of the subject simultaneously;
c) generating a right monocular illuminating beam and/or a left monocular illuminating beam;
d) optically superposing said right ocular stimulating beam and said right monocular illuminating beam in a right optical channel and/or optically superposing said left ocular stimulating beam and said left monocular illuminating beam in a left optical channel, respectively;
e) collecting the right monocular measuring beam or the left monocular measuring beam along an optical path that is the inverse of that of the right monocular illuminating beam and of the left monocular illuminating beam, respectively;
f) analyzing the right monocular measuring beam or the left monocular measuring beam so as to determine at least one right monocular vision parameter or left monocular vision parameter, respectively; and
g) repeating steps c) to f) after switching of the monocular measuring beam, so as to determine at least one binocular vision parameter of a subject using the same ocular stimulation for the right eye and left eye of the subject.

According to particular and advantageous aspects, the method for determining at least one objective binocular vision parameter of a subject according to the invention comprises carrying out the steps of the above method for a first proximity value P1, then carrying out the steps of the same method for at least one other proximity value Pn.

Advantageously, step c) of generating a right monocular illuminating beam and/or a left monocular illuminating beam is carried out by dividing or switching a single illuminating beam.

DETAILED DESCRIPTION OF AN EXAMPLE EMBODIMENT

The following description, given with regard to the appended drawings, by way of nonlimiting example, will allow what the invention consists of and how it can be carried out to be understood.

Generally, it is desirable to be able to measure correction parameters such as sphere, cylinder, axis and higher-order aberrations (see standard ISO 24157:2008, which specifies standardized methods allowing aberrations in the human eye to be reported), keratometry, corneal topography, pupil diameter, etc. with precision, generally under binocular vision conditions.

Various embodiments of the device of the invention, which allow a binocular measurement to be taken, will now be described in detail.

The principle of the device is to treat the optical paths of the visual stimulus and measurement signals differently, in order to make a single stimulus binocular, and to select an eye to be measured in alternation without mechanically moving the entire measuring instrument.

Figure 1:
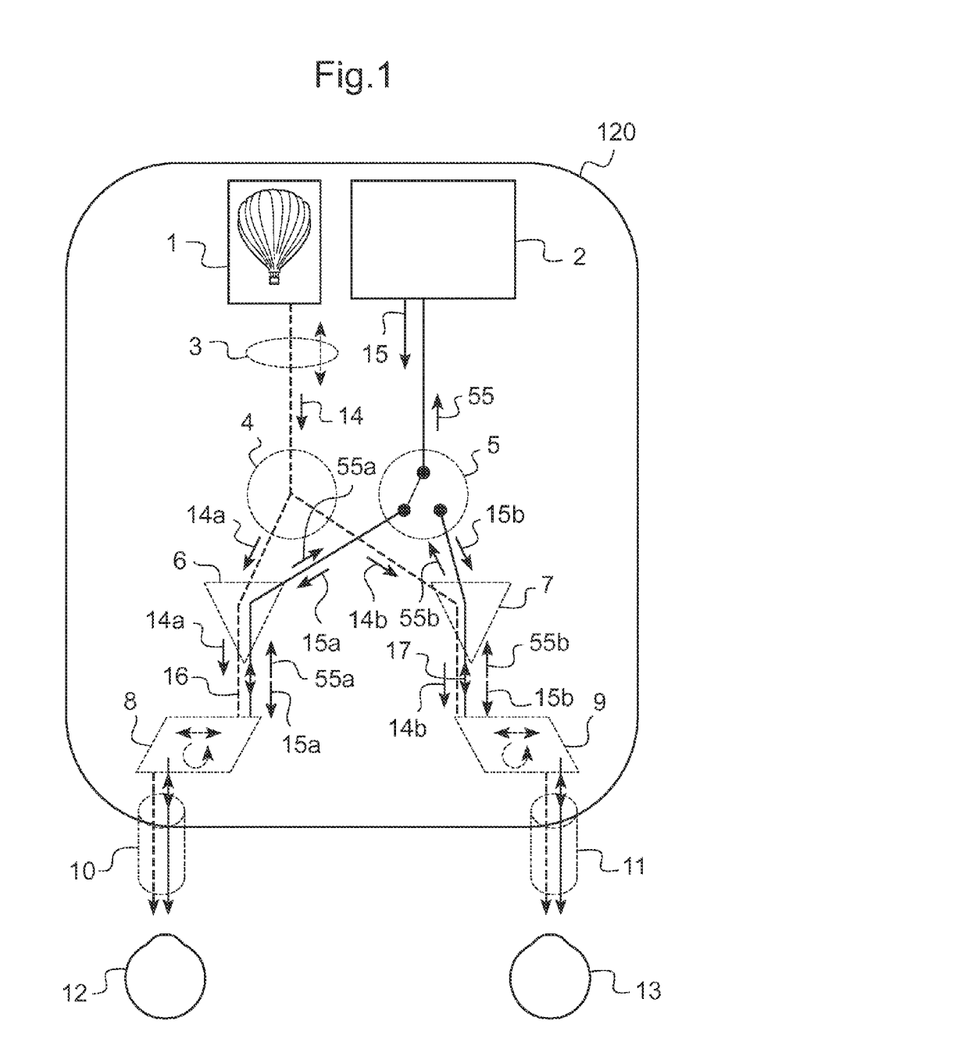
FIG. 1 schematically shows an ophthalmological instrument for taking a multiplexed binocular measurement according to a first embodiment of the invention.

FIG. 1 shows a top view of an ophthalmological instrument for taking a multiplexed binocular measurement according to a first embodiment of the invention. The ophthalmological instrument 120 in FIG. 1 incorporates, in one and the same housing (represented by a thin line) a visual stimulus 1, a measuring means 2 and a binocular multiplexing/demultiplexing system. The expression "binocular multiplexing system" is used in the rest of the present document for the sake of simplicity. The binocular ophthalmological instrument comprises a right eyepiece 11 placed facing the right eye 13 of the subject, and a left eyepiece 10 placed facing the left eye 12 of the subject. In the exit channel leading to the right eye, the instrument comprises a means 9 for making adjustments to lateral position and orientation. Likewise, in the exit channel leading to the left eye, the instrument comprises a means 8 for making adjustments to lateral position and orientation. The adjusting means 8 and 9 respectively allow the right half-pupillary distance and left half-pupillary distance to be adjusted. Advantageously, the adjusting means 8 and 9 respectively allow the left optical axis 16 and the right optical axis 17 to be moved both laterally and angularly, in order to allow adjustments to be made to the system depending on interpupillary distance and near-vision prismatic convergence. Optionally, the device may comprise adjusting means for aligning the beams depending on the height of each eye.

The binocular stimulating system of the ophthalmological binocular measuring instrument in FIG. 1 will now be described in detail. The binocular stimulating system comprises a single stimulus test pattern 1 that is common to both eyes. The stimulus test pattern 1 is illuminated by a light source so as to generate a single stimulating beam 14. An optical conjugating system 3 contributes to the formation of a stimulating image beam 14 transmitted toward the eyes 12 and 13 of the subject. Advantageously, the optical conjugating system 3 has a variable optical power, so as to allow the proximity of the stimulus test pattern 1 to be modified and the visual accommodation of the subject to be stimulated for a preset proximity value. The binocular stimulating system also comprises a beam splitter 4 placed between, on the one hand, the stimulus test pattern 1, and on the other hand, the adjusting means 8 and 9 described above. The beam splitter 4 is able to spatially split the stimulating image beam 14 into a right ocular stimulating beam 14b and a left ocular stimulating beam 14a. Advantageously, the right ocular stimulating beam 14b and the left ocular stimulating beam 14a have the same optical intensity.

In addition, the ophthalmological instrument in FIG. 1 comprises an ophthalmological measuring means 2 configured to analyze the optical properties of one eye at a time. The measuring means 2 comprises a light source able to emit an illuminating optical beam 15, and a sensor able to detect a reflected and/or refracted optical beam 55. The principle behind the ophthalmological measurement is the measurement of a beam 55 generated by reflection and/or refraction of the single illuminating optical beam 15 from the right eye 13 or from the left eye 12. Advantageously, the single illuminating optical beam 15 and the reflected and/or refracted optical beam 55 are colinear at the entrance of the measuring means 2.

The ophthalmological measuring instrument furthermore comprises an optical switch 5 having at least two positions. The optical switch 5 placed between, on the one hand, the measuring means 2, and on the other hand, the adjusting means 8 and 9 described above. The optical switch 5 is able to receive the single illuminating beam 15 and to form a right monocular illuminating beam 15b directed toward the right eye 13 of the subject, or selectively to form a left monocular illuminating beam 15a directed toward the left eye 12 of the subject (as shown in FIG. 1). The optical switch 5 functions in both propagation directions of the optical beams. When the switch 5 is in the position for illuminating the left eye 12, the optical switch 5 is able to receive a left monocular measuring beam 55a resulting from reflection and/or refraction of the illuminating beam from the left eye 12, and to transmit it toward the sensor of the measuring means 2 (see FIG. 1). When the optical switch 5 is in the position for illuminating the right eye 13, the switch 5 receives a right monocular measuring beam 55b resulting from reflection and/or refraction of the illuminating beam from the right eye 13 and transmits the right monocular measuring beam 55b toward the sensor of the measuring means 2. Thus, the optical switch 5 demultiplexes the illuminating beam and multiplexes the right and left monocular measuring beams 55b and 55a in the direction of one and the same sensor. The measuring means 2 uses a right monocular measurement and a left monocular measurement to deduce a multiplexed binocular measurement.

The ophthalmological measuring instrument also comprises an optical superposing means 6 in a left optical channel 16, and a optical superposing means 7 in a right optical channel 17, respectively. The superposing means 7 is placed between the optical beam splitter 4, the optical switch 5 and the right eyepiece 11. The superposing means 7 receives the right ocular stimulating beam 14b and the right monocular illuminating beam 15b and superposes them in the right optical channel 17 in the direction of the right eye 13. In the other propagation direction, the superposing means 7 receives the right monocular measuring beam 55b and directs it toward the optical switch 5. Analogously, the superposing means 6 is placed between the optical beam splitter 4, the optical switch 5 and the left eyepiece 10. The superposing means 6 receives the left ocular stimulating beam 14a and the left monocular illuminating beam 15a and superposes them in the left optical channel 16 in the direction of the left eye 12. In the other propagation direction, the superposing means 6 receives the left monocular measuring beam 55a and directs it toward the optical switch 5. It may be seen that the ocular stimulating beam 14, 14a, 14b does not pass through the optical switch 5. The optical superposing means 6 and 7 make it possible to ensure that the two eyes are permanently stimulated by the right and left ocular stimulating beams 14b and 14a, whereas the reflection and/or refraction measurement is carried out for one eye at a time, depending on the position of the optical switch 5. In this way, the visual stimulation is always binocular whereas the two left and right monocular measurements are carried out one after the other.

The optical system 3 placed between the stimulus test pattern 1 and the beam splitter 4 for example allows the average sphere error of the two eyes 12, 13 to be corrected in order to improve the sharpness and the fusion of the stimulus. Advantageously, the optical system 3 has the effect of making the angular size of the stimulus constant and independent of vergence.

Figure 2:
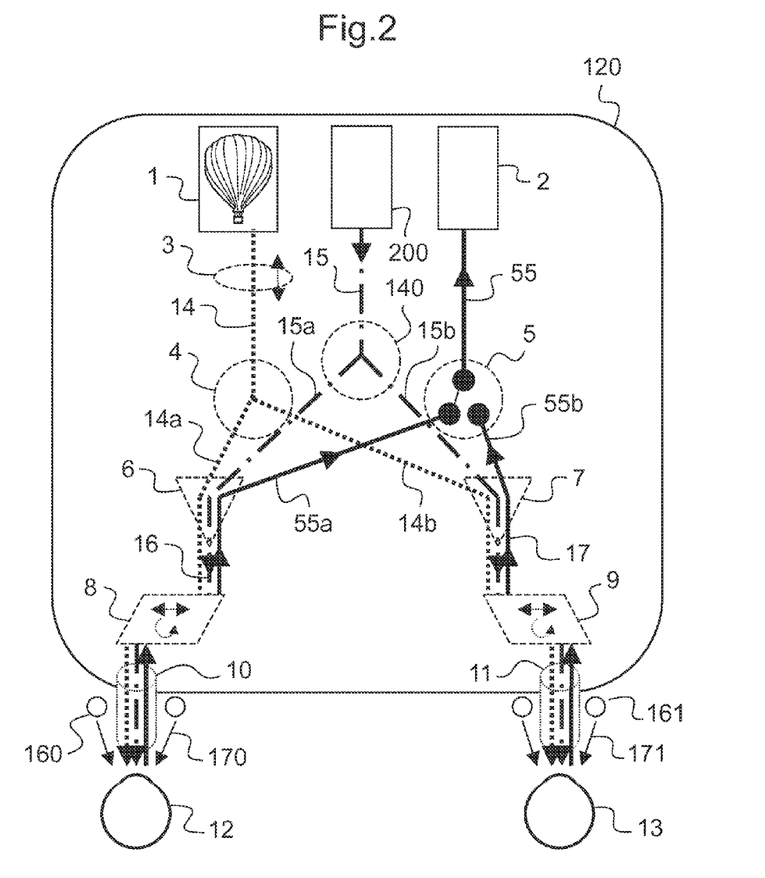
FIG. 2 schematically shows an ophthalmological instrument for taking a multiplexed binocular measurement according to a first variant of the first embodiment of the invention.

FIG. 2 shows a top view of an ophthalmological instrument for taking a multiplexed binocular measurement according to a first variant of the first embodiment of the invention. The same elements are designated by the same reference numbers as in FIG. 1. The ophthalmological instrument 120 in FIG. 2 incorporates, in one and the same housing (represented by a thin line) a visual stimulus 1, a measuring means 2, an illuminating means 200 and a binocular multiplexing system. The binocular ophthalmological instrument comprises a right eyepiece 11 placed facing the right eye 13 of the subject, and a left eyepiece 10 placed facing the left eye 12 of the subject. In the exit channel leading to the right eye, the instrument comprises a means 9 for making adjustments to lateral position and orientation. Likewise, in the exit channel leading to the left eye, the instrument comprises a means 8 for making adjustments to lateral position and orientation. The adjusting means 8 and 9 respectively allow the right half-pupillary distance and left half-pupillary distance to be adjusted. Advantageously, the adjusting means 8 and 9 respectively allow the left optical channel 16 and the right optical channel 17 to be moved both laterally and angularly, in order to allow adjustments to be made to the system depending on interpupillary distance, near-vision prismatic convergence, and the height of the two eyes.

The binocular stimulating system of the ophthalmological binocular measuring instrument in FIG. 2 will now be described in detail. The binocular stimulating system comprises a single stimulus test pattern 1 that is common to both eyes. The stimulus test pattern 1 is illuminated by a light source so as to generate a single stimulating beam 14. An optical conjugating system 3 contributes to the formation of a stimulating image beam 14 transmitted toward the eyes 12 and 13 of the patient. Advantageously, the optical conjugating system 3 has a variable optical power, so as to allow the proximity of the stimulus test pattern 1 to be modified and the visual accommodation of the subject to be stimulated for a preset proximity value. The binocular stimulating system also comprises a beam splitter 4 placed between, on the one hand, the stimulus test pattern 1, and on the other hand, the adjusting means 8 and 9 described above. The beam splitter 4 is able to spatially split the stimulating image beam 14 into a right ocular stimulating beam 14b and a left ocular stimulating beam 14a. Advantageously, the right ocular stimulating beam 14b and the left ocular stimulating beam 14a have the same optical intensity.

In addition, the ophthalmological instrument in FIG. 2 comprises an illuminating light source 200 able to emit a binocular illuminating optical beam 15. The binocular illuminating system also comprises a beam splitter 140 placed between, on the one hand, the illuminating light source 200, and on the other hand, the adjusting means 8 and 9 described above. The beam splitter 140 is able to spatially split the illuminating beam 15 into a right ocular illuminating beam 15b and a left ocular illuminating beam 15a. Advantageously, the right ocular illuminating beam 15b and the left ocular illuminating beam 15a have the same optical intensity. The two right and left ocular illuminating beams 15b and 15a are able to illuminate both eyes simultaneously, whereas the measurement is only carried out on one eye at a time.

In addition, the ophthalmological instrument in FIG. 2 comprises an ophthalmological measuring means 2 configured to analyze the optical properties of one eye at a time. The measuring means 2 comprises a sensor able to detect a reflected and/or refracted optical beam 55. The principle behind the ophthalmological measurement is the measurement of a beam 55 generated by reflection and/or refraction of the illuminating optical beam 15 seen by the two eyes 12 and 13.

The ophthalmological measuring instrument furthermore comprises an optical switch 5 having at least two positions. When the switch 5 is in the position for measuring the left eye 12, the optical switch 5 is able to receive a monocular measuring beam 55a originating from the left eye 12, and to transmit it toward the sensor of the measuring means 2 (see FIG. 2). When the optical switch 5 is in the position for measuring the right eye 13, the switch 5 receives a measuring beam 55b from the right eye 13 and transmits the right monocular measuring beam 55b toward the sensor of the measuring means 2. The optical switch 5 multiplexes the right and left monocular measuring beams 55b and 55a in the direction of one and the same sensor. The measuring means 2 uses a right monocular measurement and a left monocular measurement to deduce a multiplexed binocular measurement.

The ophthalmological measuring instrument also comprises an optical superposing means 6 in a left optical channel 16, and a optical superposing means 7 in a right optical channel 17, respectively. The superposing means 7 is placed between the optical stimulating-beam splitter 4, the optical illuminating-beam splitter 140, the optical switch 5 and the right eyepiece 11. The superposing means 7 receives the right ocular stimulating beam 14b and the right ocular illuminating beam 15b and superposes them in the right optical channel 17 in the direction of the right eye 13. In the other propagation direction, the superposing means 7 receives the right monocular measuring beam 55b and directs it toward the optical switch 5. Analogously, the superposing means 6 is placed between the optical stimulating-beam splitter 4, the optical illuminating-beam splitter 140, the optical switch 5 and the left eyepiece 10. The superposing means 6 receives the left ocular stimulating beam 14a and the right ocular illuminating beam 15b and superposes them in the left optical channel 16 in the direction of the left eye 12. In the other propagation direction, the superposing means 6 receives the left monocular measuring beam 55a and directs it toward the optical switch 5. It may be seen that the ocular stimulating beam 14, 14a, 14b and the illuminating beam 15, 15a, 15b do not pass through the optical switch 5. The optical superposing means 6 and 7 make it possible to ensure that the two eyes are permanently stimulated and illuminated by the right and left ocular stimulating beams 14b and 14a and the right and left illuminating beams 15b and 15a, whereas the reflection and/or refraction measurement is carried out for one eye at a time, depending on the position of the optical switch 5. In this way, the visual stimulation and the illumination are always binocular whereas the two left and right monocular measurements are carried out one after the other.

The optical system 3 placed between the stimulus test pattern 1 and the beam splitter 4 for example allows the average sphere error of the two eyes 12, 13 to be corrected in order to improve the sharpness and the fusion of the stimulus. Advantageously, the optical system 3 has the effect of making the angular size of the stimulus constant and independent of vergence.

In addition, the left and right exit pupils 10 and 11 of the system in FIG. 2 may be equipped with illuminating sources 160 and 161, respectively, in order to carry out an analysis of the cornea, such as for example by keratometry or corneal topography. These illuminating sources 160 and 161 emit a light beam 170 and 171, respectively, in the direction of the cornea of each eye 12 and 13. The measurement is taken by the measuring means 2 via the measuring beams 55a and 55b depending on the state of the switch 5.

Figure 3:
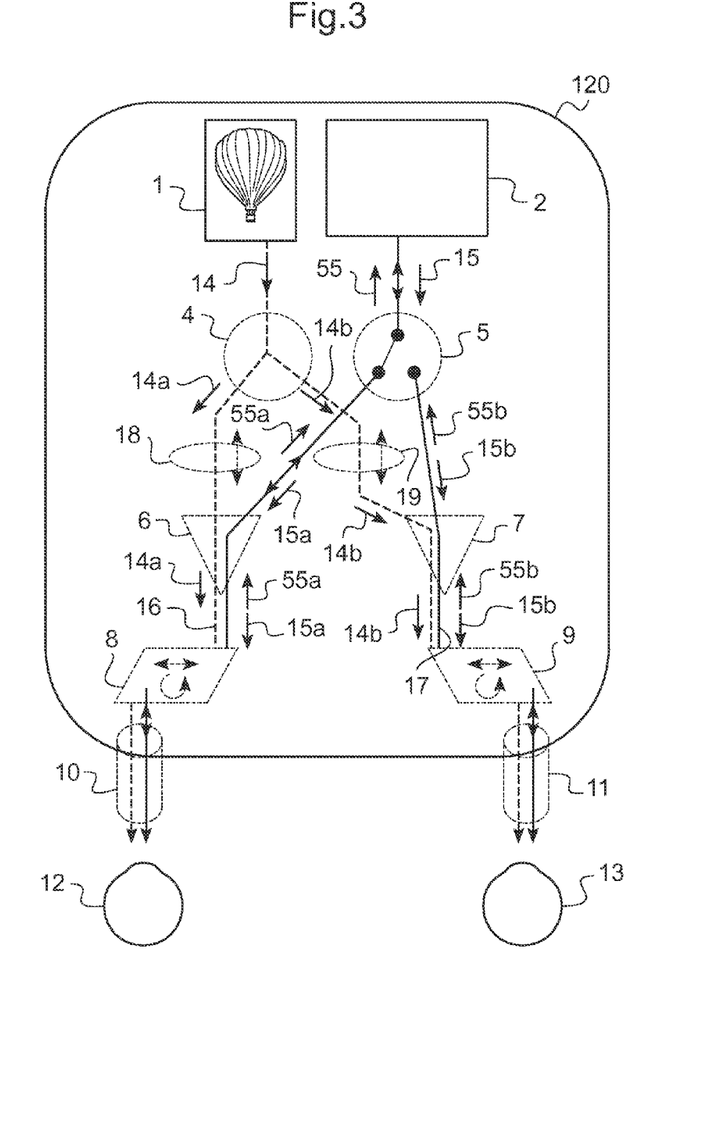
FIG. 3 schematically shows an ophthalmological instrument for taking a multiplexed binocular measurement according to a second variant of the first embodiment of the invention.

FIG. 3 shows a second variant of the ophthalmological measuring instrument in FIG. 1. In this second variant the optical system 3 placed in front of the stimulus test pattern 1 has been replaced by two optical systems 18 and 19. The optical system 18 is placed between the optical beam splitter 4 and the superposing optical means 6 in the left optical channel. Symmetrically, the optical system 19 is placed between the optical beam splitter 4 and the superposing optical means 7 in the right optical channel. The optical systems 18 and 19 allow the sphere and/or cylinder error of each eye to be corrected independently. Advantageously, the optical systems 18 and 19 also allow the shifts in optical distance created by the optical means 8 and 9 during the interpupillary adjustment and the prismatic convergence to be compensated for.

The multiplexed binocular ophthalmological measuring instrument can be employed with a wide range of existing monocular ophthalmological measuring apparatuses. The optical switch 5 makes it possible to rapidly and discretely change the measuring channel between the two eyes. Firstly, the pupillary distance is adjustable. In addition, the stimulation is permanently binocular. The reflection and/or refraction measurement is carried out for each eye on its sight axis. The convergence of the gaze is thus taken into account, for example when taking a near-vision measurement.

Treating the stimulus channel (visible light) and the measuring channel (infrared light) separately avoids using specific optics in a spectral band.

Another embodiment of the invention makes use of the monocular stimulus and monocular measuring system of an external apparatus. The monocular apparatus is combined with a binocular multiplexing device in order to transform the monocular stimulus into a binocular stimulus and to select the eye to be measured.

Figure 4:
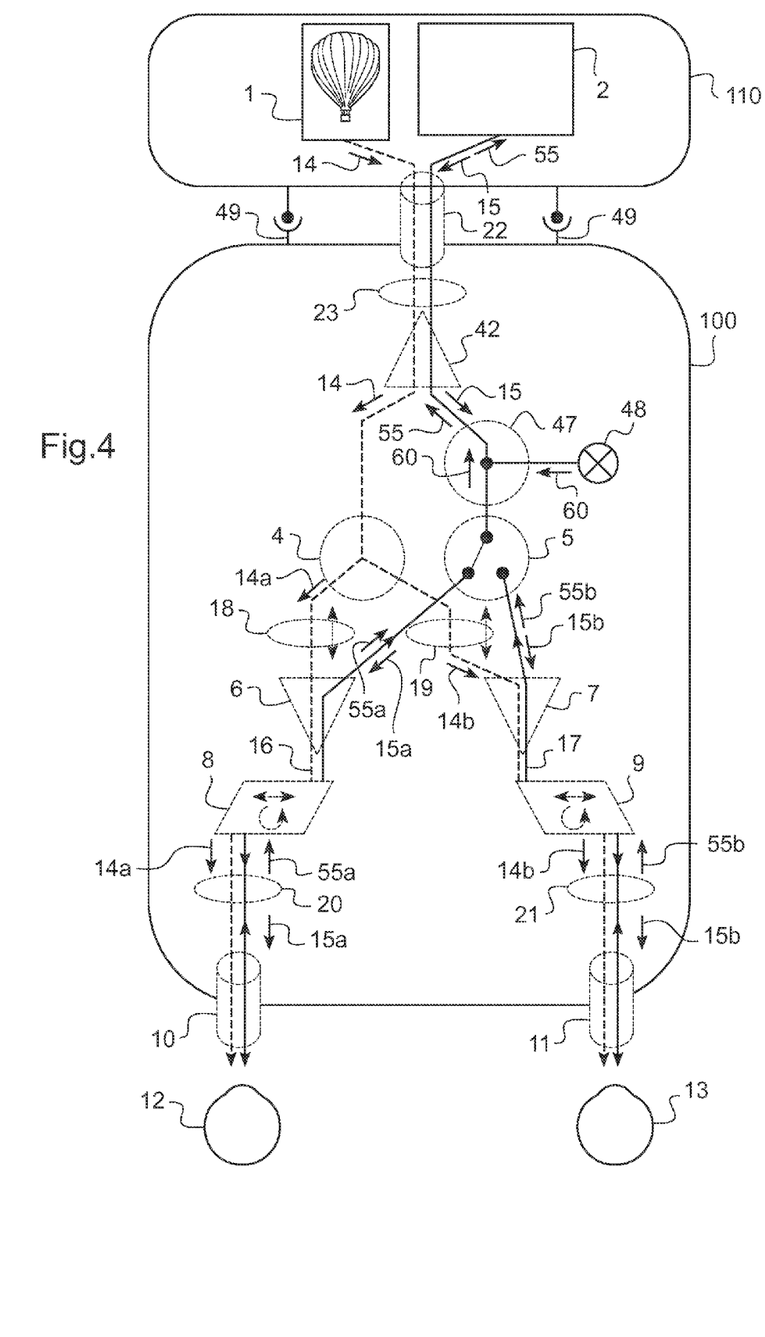
FIG. 4 schematically shows a binocular multiplexing device according to a second embodiment of the invention.

FIG. 4 schematically shows a monocular apparatus 110 coupled to a binocular multiplexing device 100 according to a second preferred embodiment of the invention. In FIG. 4, elements that are the same as those described with regard to FIGS. 1 to 3 have been designated by the same reference signs. The external apparatus 110 comprises a stimulus test pattern 1 and a measuring means 2 and at least one optical channel 22. The measuring means 2 comprises a light source able to emit an illuminating optical beam 15, and a sensor able to detect a reflected and/or refracted optical beam 55. The stimulus test pattern 1 is illuminated by a light source so as to generate a single stimulating beam 14. The optical channel 22 is able to let the stimulating beam 14 and the illuminating beam 15 pass, and to receive the reflected and/or refracted measuring beam 55. The binocular multiplexing device 100 comprises a right eyepiece 11, a left eyepiece 10, a means 9 for adjusting lateral position and orientation in the exit channel toward the right eye, and a means 8 for adjusting lateral position and orientation in the exit channel toward the left eye. The binocular multiplexing device 100 also comprises:

a beam splitter 4 for spatially splitting a single stimulating image beam 14 into a right ocular stimulating beam 14b and a left ocular stimulating beam 14a;

an optical switch 5 for selectively orienting the measurement signal toward the right eye or toward the left eye;

an optical beam-combining means 6 in the left optical channel 16, and an optical beam-combining means 7 in the right optical channel 17, respectively.

The optical switch 5 and the optical superposing means 6 and 7 have the same functions and operate analogously to the corresponding elements described with regard to FIG. 1. The binocular multiplexing device 100 furthermore comprises:

an optical beam splitter 42 placed, on the one hand, between the optical channel 22 of the external apparatus, and on the other hand, the optical switch 5 and the first beam splitter 4;

an optical entrance system 23, a right optical exit system 21 and a left optical exit system 20;

an alignment test pattern 48 and another beam splitter 47 placed between the beam splitter 42 and the optical switch 5;

fasteners 49 for holding the external measuring instrument 110 and the binocular multiplexing device 100 together once the optical alignment has been carried out;

a system against which the forehead can press and a chin rest for holding the head of the subject in a set posture, or fastening points suitable for receiving a standard (artificial eye), and compatible with existing apparatuses.

The beam splitter 42 allows the single stimulating image beam 14 issued from the stimulus test pattern 1 and the illuminating beam 55 issued from the measuring system 2 to be split, these two beams, 14 and 22, arriving from the same optical channel 22. The entrance optical system 23 is placed between the optical channel 22 and the beam splitter 42. The right optical exit system 21 is placed between the optical adjusting means 9 and the right optical exit channel 11. The left optical exit system 20 is placed between the optical adjusting means 8 and the left optical exit channel 10. Together, the optical systems 23, 20 and 21 allow an image of the eyes 12, 13 to be formed in the entrance optical channel 22 through the exit optical channels 10, 11. Advantageously, the alignment test pattern may be a standard such as an artificial eye, the refraction values of which are known. The alignment test pattern 48 emits an aligning optical beam 60. The alignment test pattern 48 is imaged in the measuring optical channel of the external apparatus by virtue of the beam splitters 47 and 42. The alignment test pattern 48 is used to adjust the position of the exit pupil of the external apparatus 110 opposite the entrance pupil of the binocular multiplexing device 100. The alignment test pattern 48 is also used as a centering reference during the adjustment of the pupillary distances. The alignment test pattern 48 emits an aligning optical beam 60 only during the optical adjustment between the external measuring apparatus and the multiplexing device. During the measurements of ocular reflection and/or refraction, the alignment test pattern 48 is turned off.

A binocular multiplexing device such as shown in FIG. 4 has many advantages. Firstly, the binocular multiplexing device 100 can be employed with a wide range of existing monocular apparatuses without it being necessary to make modifications to the monocular measuring apparatus 110. As detailed above, the binocular multiplexing device 100 makes it possible to rapidly and discretely change the measuring channel between the two eyes. In addition, each eye is measured along its sight axis, thereby allowing the convergence of the gaze to be taken into account. Lastly, the pupillary distance is adjustable. Advantageously, treating the stimulus channel (visible light) and the measuring channel (infrared light) separately avoids using specific optics in a limited spectral band.

Figure 5:
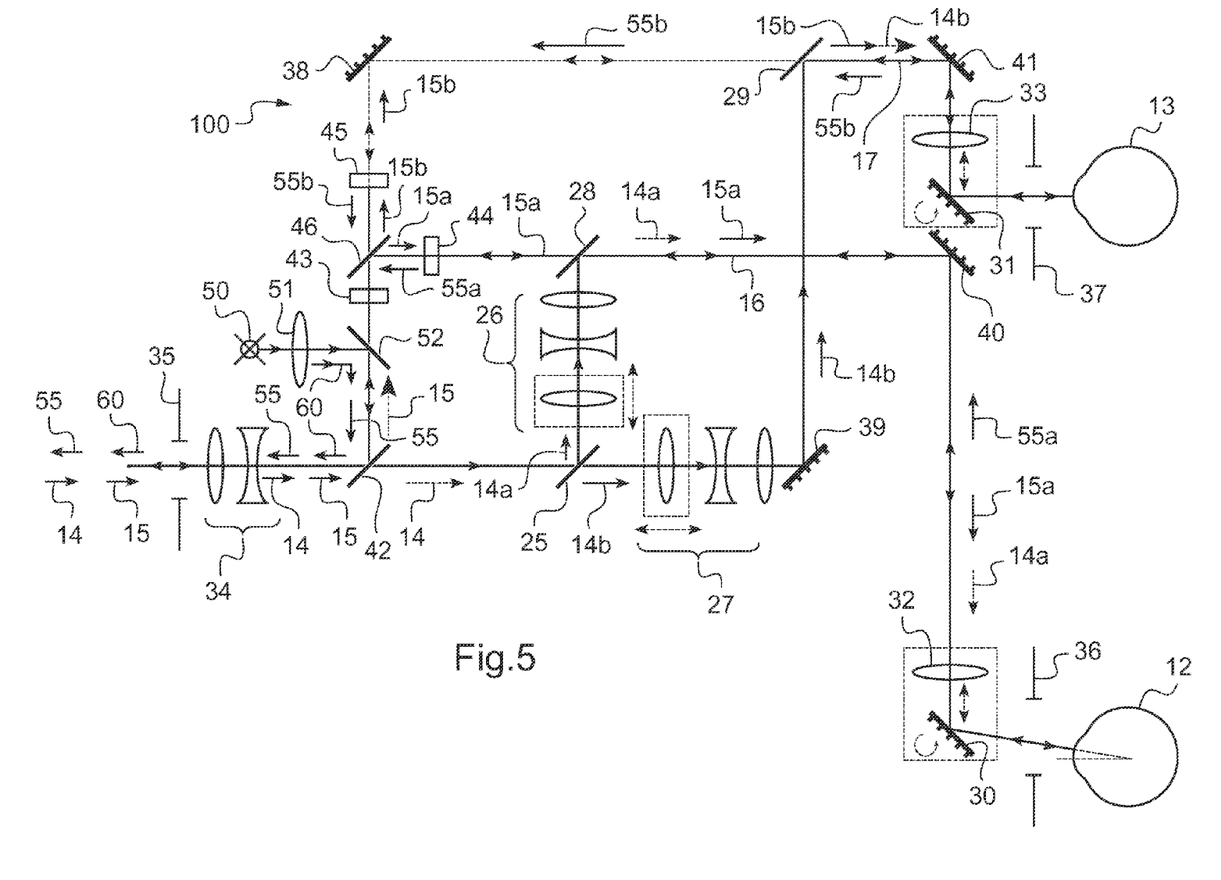
FIG. 5 schematically shows a binocular multiplexing device according to a third embodiment of the invention.
Figure 6:
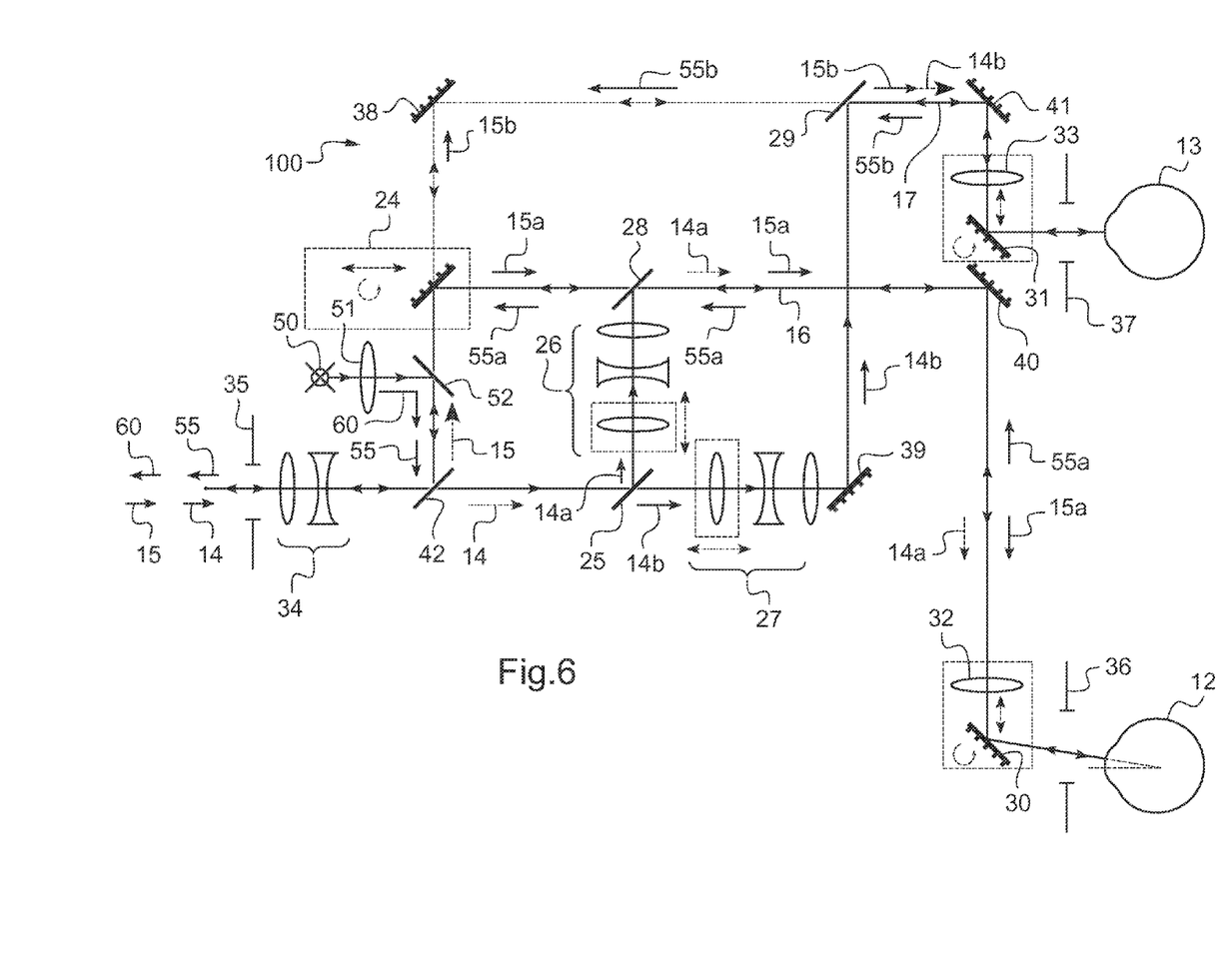
FIG. 6 schematically shows a binocular multiplexing device according to a third embodiment of the invention.

FIGS. 5 and 6 schematically show a binocular multiplexing device 100 according to two variants of a third embodiment of the invention. The binocular multiplexing device 100 in FIG. 5 or in FIG. 6 is intended to be placed opposite the optical channel of a monocular measuring apparatus comprising a stimulus test pattern and a measuring means. In FIGS. 5 and 6, the stimulus test pattern and the measuring means are not shown. The binocular multiplexing device 100 comprises an entrance pupil 35 that is intended to be connected to an external monocular measuring apparatus. A first optical system 34 is placed at the entrance of the binocular multiplexing device 100. The optical system 34 is able to receive a stimulating image beam 14 and/or a monocular illuminating beam 15 originating from the external monocular measuring apparatus. In the other direction, the optical system 34 is able to receive a measuring beam 55 either originating from the right eye or the left eye of the subject, and to transmit this measuring beam toward the external monocular measuring apparatus. A first beam-splitting plate 42 is placed on the optical path of the stimulating and illuminating beams 14 and 15, downstream of the optical system 34. The first beam-splitting plate 42 spatially splits the optical channels of the stimulating and measuring signals. In the embodiment shown in FIG. 5, the stimulating beam 14 passes through the beam-splitting plate 42 whereas the illuminating beam 15 is reflected by the beam-splitting plate 42. Advantageously, the beam-splitting plate 42 is a dichroic plate, having a surface treatment able to split, on the one hand, the stimulating beam 14 in the visible (between about 400 and 700 nm) and, on the other hand, the illuminating beam 15 and the measuring beam 55 in the infrared (the near infrared being between about 750 nm and 1000 nm). A hot mirror, which lets visible light pass but reflects in the infrared, may for example be used. Alternatively, a cold mirror, which lets infrared light pass but reflects in the visible, may be used. A second beam-splitting plate 25 (or beam-splitting cube) is placed on the optical path of the stimulating image beam 14 downstream of the first beam-splitting plate 42. The second beam-splitting plate 25 spatially divides the stimulating image beam 14 into a right ocular stimulating beam 14b directed toward the right eye 13 and a left ocular stimulating beam 14a directed toward the left eye 12 of the subject. In the right ocular stimulating channel and the left ocular stimulating channel, respectively, lenses 27 and 26, respectively, arranged in a Badal optical system, allow the vision of the stimulus to be corrected for right-eye and left-eye sphere error, respectively. Advantageously, the angular size of the stimulus is independent of its position. It is therefore possible to increase or decrease the distance (vergence and convergence) of the eye from the stimulus without changing the angular size thereof.

In FIG. 5, a first polarizing element 43 and a third beam-splitting plate 46 are placed on the optical path of the illuminating beam 15 downstream of the first beam-splitting plate 42. The polarizing element 43 is a polarizing element having a variable polarizing axis, which element is able to receive the illuminating beam 15 and to modify the polarization axis of the transmitted beam. Advantageously, an electrically controlled liquid-crystal polarizing element 43 is used the polarization axis of which is orientable via the application of an electrical voltage. Alternatively, the polarizing element 43 may be a rotatably mounted polarizer. In the case where the light source is polarized, the polarizing element 43 may be replaced by a means able to rotate the polarization axis of the source. The third beam-splitting plate 46 (or beam-splitting cube) is placed on the optical path of the illuminating beam 15 downstream of the polarizing element 43. The third beam-splitting plate 46 is able to divide the illuminating beam 15 and to form a right monocular illuminating beam 15b intended to illuminate the right eye 13 of the subject and/or to form a left monocular illuminating beam 15a intended to illuminate the left eye 12 of the subject. A second polarizing element 44 is placed on the optical path of the left monocular illuminating beam 15a downstream of the first polarizing element 43 and of the third beam-splitting plate 46. A third polarizing element 45 is placed on the optical path of the right monocular illuminating beam 15b downstream of the first polarizing element 43 and of the third beam-splitting plate 46. The polarization axes of the second and third polarizing elements 44 and 45 are crossed one relative to the other. The second and third polarizing elements 44 and 45 are for example linear polarizers. Alternatively, a single splitting element may combine the splitting function of the beam-splitting plate 46 and the polarizing function of the polarizing elements 44 and 45. In a first measuring position, the polarization axis of the first polarizing element 43 is aligned with the polarization axis of the first polarizing element 44 and crossed with the polarization axis of the third polarizing element 45. In a second measuring position, the polarization axis of the first polarizing element 43 is aligned with the polarization axis of the third polarizing element 45 and crossed with the polarization axis of the second polarizing element 44. In this way, only one of the two monocular illuminating beams, the left beam 15a or right beam 15b, respectively, is active whereas the other monocular illuminating beam is turned off. In other words, by modifying the orientation of the polarization axis of the polarizing element 43 in order to align it with the axis of one or other of the polarizing elements 44 and 45, the illuminating beam is switched from one eye to the other. The elements 43, 44, 45 and 46 thus form an optical switch able to select in alternation one of the two eyes for a monocular measurement. It will be noted that the stimulating beams 14, 14a, 14b do not pass through the switching device formed by the elements 43, 44, 45 and 46. Thus, the left and right ocular stimulating beams 14a and 14b are permanently and simultaneously active so as to stimulate the binocular vision of the subject.

In FIG. 6, as a variant of the device in FIG. 5, the polarizing elements 43, 44, 45 and the third beam-splitting plate 46 are replaced by an orientable mirror 24 that can be oriented so as to select one of the two optical measuring channels.

In FIGS. 5 and 6, provision is thus made for a right ocular stimulating beam 14b and a left ocular stimulating beam 14a, and for a right monocular illuminating beam 15b or a left monocular illuminating beam 15a. A fourth beam-splitting plate 28 is placed on the optical path of the left monocular illuminating beam 15a, downstream of the second beam-splitting plate 25, and on the optical path of the left ocular stimulating beam 14a, downstream of the second polarizing element 44. The fourth beam-splitting plate 28 allows the left monocular illuminating beam 15a and the left ocular stimulating beam 14a to be combined in one and the same left optical channel 16. In one embodiment, the fourth beam-splitting plate 28 is a dichroic plate having a surface treatment designed to allow the left ocular stimulating beam 14a in the visible domain and the left monocular illuminating beam 15a in the infrared domain to be recombined (and in the reverse direction, designed to transmit the left monocular measuring beam 55a on the same optical path as the left monocular illuminating beam 15a). The beam-splitting plate 28 may be a cold mirror or a hot mirror as explained above. Likewise, a fifth beam-splitting plate 29 is placed on the optical path of the right monocular illuminating beam 15b, downstream of the second beam-splitting plate 25, and on the optical path of the right ocular stimulating beam 14b, downstream of the third polarizing element 45. The fifth beam-splitting plate 29 allows the right monocular illuminating beam 15b and the right ocular stimulating beam 14b to be combined in one and the same right optical channel 17. In one embodiment, the fifth beam-splitting plate 29 is also a cold mirror having a surface treatment designed to allow the right ocular stimulating beam 14b in the visible domain and the right monocular illuminating beam 15b in the infrared domain to be recombined (and in the reverse direction, designed to transmit the right monocular measuring beam 55b on the same optical path as the right monocular illuminating beam 15b). Advantageously, the infrared beam is transmitted by the splitting cold mirror, 28 or 29, respectively, whereas the visible beam is reflected by the cold mirror. The cold mirror, 28 or 29, respectively, thus rejoins the optical axis of the ocular stimulating beam and the optical axis of the measuring beam of each eye. This combination makes it possible to take measurements, and especially near-vision measurements, on the sight axis of each eye, the subject being in a binocular vision position since, as indicated above, the two right and left ocular stimulating beams 14b and 14a are seen simultaneously by the subject.

Mirrors 40, 41 serve to redirect the optical path of the recombined optical channels, 16 and 17 respectively, for each eye. An optical system composed of a lens 32 and a mirror 30 allows the left optical channel 16 to be aligned with the sight axis of the left eye 12. Analogously, an optical system composed of a lens 33 and a mirror 31 allows the left optical channel 16 to be aligned with the sight axis of the left eye 12. The mirrors 30, 31 may also be used to adjust the half-pupillary distance. The optical pulse of the two channels 16 and 17 are calibrated to be the same optical length. The exit mirrors 30 and 31 may be moved translationally and oriented so that the measuring optical axis is centered on the pupil of each eye, taking into account pupillary distance and the convergence of the eyes.

The optical system of lenses 34 placed in front of the entrance pupil 35, and an auxiliary lens 32, 33 placed in front of an exit pupil, 36 and 37, respectively, are used in order to image each eye in the same optical position, as defined by the monocular apparatus. The auxiliary lenses 32, 33 move conjointly with the associated exit mirror 30, 31 so as to correct optical path differences between the right optical channel 17 and the left optical channel 16.

When the eyes 12, 13 of the subject are aligned opposite the exit pupils of the binocular multiplexing apparatus, each eye 12, 13 permanently receives an ocular stimulating beam 14a and 14b, respectively. Depending on the position of the polarizing element 43, the right eye 13 receives a right monocular illuminating beam 15b or the left eye 12 receives a left monocular illuminating beam 15a. The right monocular illuminating beam 15b is reflected and/or refracted from the right eye 13 and forms a right ocular measuring beam 55b. Alternatively, the left monocular illuminating beam 15a is reflected and/or refracted from the left eye 12 and forms a left ocular measuring beam 55a. The right ocular measuring beam 55b follows the same optical path as the right monocular illuminating beam 15b in the right optical channel 17, from the right eye 13 as far as the third beam-splitting plate 46. Likewise, the left ocular measuring beam 55a follows the same optical path as the left monocular illuminating beam 15a in the left optical channel 16, from the left eye 12 as far as the third beam-splitting plate 46. Depending on the position of the polarizing element 43, the right optical channel 17 or the left optical channel 16 is activated for the measurement. The system composed of the polarizing elements 43, 44 and 45 functions reciprocally for the right and left ocular measuring beams 55b and 55a.

It will be recalled that, in the first measuring position, the polarization axis of the first polarizing element 43 is oriented parallel to the polarization axis of the second polarizing element 44 and perpendicularly to the polarization axis of the third polarizing element 45. In the second measuring position, the polarization axis of the first polarizing element 43 is oriented parallel to the polarization axis of the third polarizing element 45 and perpendicularly to the polarization axis of the second polarizing element 44. In this way, only one of the two ocular measuring beams is transmitted, the right beam 55b or the left beam 55a, respectively, whereas the other monocular illuminating beam and the other measuring beam are blocked. In other words, by modifying the orientation of the polarization axis of the polarizing element 43 in order to align it with the axis of one or other of the polarizing elements 45 and 44, the right or left ocular measuring beam, 55b or 55a, is switched in the direction of the external monocular measuring apparatus. The elements 43, 44, 45 and 46 simultaneously switch the illuminating beam and the measuring beam. On exiting from the polarizing element 43, the measuring beam 55 (which either corresponds to the right ocular measuring beam 55b or to the left ocular measuring beam 55a) follows the inverse optical path of the monocular illuminating beam 15 and is reflected by the first beam-splitting plate 42 in the direction of the external apparatus. Thus, the device 100 allows the right and left measuring channels to be demultiplexed.

The binocular multiplexing device 100 in FIG. 5 also comprises an infrared alignment test pattern 50 and a lens 51 able to generate an optical aligning beam 60 for forming an image of the optical alignment test pattern 50. Advantageously, the optical alignment test pattern 50 may comprise a standard such as an artificial eye, the refraction values of which are known. A sixth beam-splitting plate 52 is placed between the first beam-splitting plate 42 and the first polarizing element 43. The sixth beam-splitting plate 52 recombines the optical aligning beam 60 in the channel of the single illuminating beam 15 and directs said beams toward the entrance pupil 35 of the binocular multiplexing system. The alignment test pattern 50 is used to adjust the position of the exit pupil of the external monocular apparatus opposite the entrance pupil 35 of the demultiplexer. The image of the alignment test pattern 50 is optically conjugated with the eyes of the subject 12, 13 so as to adjust the focus of the monocular apparatus. The image of the alignment test pattern 50 is also used as a centering reference during the adjustment of the pupillary distances. Advantageously, the lenses 32, 33, 34, 51 in the measuring channel (infrared light) will be given an antireflection treatment in the infrared, in order to prevent parasitic reflections.

Other technical solutions may be used to demultiplex the measuring channel. In FIG. 6, the same elements are designated by the same reference numbers as in FIG. 5. As a variant of the device in FIG. 5, the polarizing elements 43, 44, 45 and the third beam-splitting plate 46 could be replaced by an orientable mirror 24 that can be oriented so as to select one of the two optical measuring channels. According to other variants of the same embodiment, another opto-mechanical, opto-electronic, acoustic or thermal element may also be used to select one of the two channels in the context of the present invention.

Operating Mode and Operation of the System:

1. The practitioner positions the exit pupil of a monocular ophthalmological measuring apparatus opposite the entrance pupil 35 of the binocular multiplexing/demultiplexing device. To do this, he/she activates the alignment test pattern 50 then moves the monocular apparatus vertically and horizontally until the alignment test pattern 50 of the demultiplexer is centered on his/her control screen. Next, the practitioner adjusts the focus on the test pattern, which represents the virtual position of the eye. Once these adjustments have been carried out, the practitioner fastens the demultiplexer to the monocular apparatus via the fasteners 49 (suckers, Velcro, magnets, etc.)

2. The subject positions himself/herself in front of the exit pupils 36, 37 of the binocular multiplexing/demultiplexing device. The practitioner then adjusts the pupillary distances. To do this, the stimulus test pattern 1 of the monocular apparatus is placed at infinity in order to prevent the eyes from converging. Next, the practitioner selects an eye to be measured by virtue of the optical switching means 43 or 24. Next, the practitioner moves the mirror/lens assembly 30, 32 so that the pupil of the eye 12 is centered with the alignment test pattern 50. The same operation is reiterated by moving the lens/mirror assembly 31, 33 for the other eye 13.

3. The practitioner initializes the values of the sought-after ophthalmological parameter by inputting a prescription or a prior measurement or even by carrying out a far-vision first measurement. An ametropic subject will not see the stimulus clearly during this first measurement. The practitioner selects an eye to be measured by virtue of the optical switching means 43 or 24, carries out a far-vision first measurement on the selected eye, then changes eye and carries out the far-vision first measurement on the other eye. Thus a far-vision binocular first measurement is obtained.

4. Using this initial value obtained from a first measurement or from a prior measurement, the practitioner either corrects the average sphere of the two eyes or the sphere and/or the cylinder of each eye by virtue of the Badal and/or cross-cylinder optical systems 26, 27.

5. It is preferable for the practitioner to carry out a new far-vision measurement once the stimulus can be clearly seen by the subject.

6. For intermediate or near vision, the image of the stimulus test pattern is positioned at a known optical distance allowing, depending on the pupillary distance of the subject, the system to be positioned on the prismatic convergence axis of each eye by moving and orienting the exit mirrors 30, 31. The operating mode used for intermediate-vision or near-vision binocular measurements is the same as for far-vision measurements.

The binocular multiplexing device and method of the invention allow a given visual stimulus to be transmitted to both eyes simultaneously, thereby allowing an ocular reflection and/or refraction measurement that takes the convergence of the gaze into account to be carried out. The device measures only one eye at a time, but is capable of instantaneously switching the optical measuring channel from one eye to the other. Advantageously, the device of the invention comprises means for adjusting the system beforehand depending on the pupillary distance of the subject. In the case of an external stimulus and measuring means, the multiplexing device allows the two channels to be separated so that they can be processed independently.

The invention allows the refraction of an eye to the measured with a binocular stimulation from a single measuring means and a single stimulus. The device of the invention makes measurement on the sight axis of the eye possible while taking into account near-vision prismatic convergence. With the device of the invention, it is possible to select the eye to be measured while maintaining a binocular stimulus, and there is no mechanical movement during the change of eye.

The invention is particularly suitable for anyone who takes refraction-based ophthalmological measurements and who wants to provide or carry out binocular measurements.

The device of the invention may be used by an optometrist or an ophthalmologist, or even by an optician to determine parameters for personalizing spectacle lenses.

The invention claimed is:

1. A binocular multiplexing device (100) for an ophthalmological instrument (110) having a single channel for objective measurement of at least one visual parameter of a subject, said ophthalmological instrument comprising means for generating a single illuminating beam (15), means for collecting a measuring beam (55) generated by reflection and/or refraction of said illuminating beam from an eye of the subject, and a sensor associated with said single measuring channel, said binocular multiplexing device comprising:

first optical splitting means (4, 25) able to receive a stimulating image beam (14) issued from a stimulus test pattern and intended to stimulate accommodation by the subject, said first optical splitting means (4, 25) being able to split said stimulating image beam (14) into a right ocular stimulating beam (14a) and a left ocular stimulating beam (14a) so as to stimulate accommodation by the right eye (13) and left eye (12) of the subject simultaneously;

second optical splitting means (5, 140, 24, 43, 44, 45, 46) able to receive said single illuminating beam (15) and to split said single illuminating beam (15) into a right monocular illuminating beam (15b) and a left monocular illuminating beam (15a), said right monocular illuminating beam (15b) and left monocular illuminating beam (15a) being intended to illuminate the right eye (13) and the left eye (12) of the subject, respectively, in order to form, after reflection and/or refraction from the eye (12, 13) in question, a right ocular measuring beam (55b) and a left ocular measuring beam (55a), respectively;

optical switching means (5, 24, 43, 44, 45, 46) able to receive said right ocular measuring beam (55b) and said left ocular measuring beam (55a) and to steer in sequence said right ocular measuring beam (55b) and said left ocular measuring beam (55a) into said single measuring channel, respectively;

first optical combining means (7, 29) able to superpose the right ocular stimulating beam (14b) and the right monocular illuminating beam (15b), and first optical means for directing the right ocular stimulating beam (14b) and the right monocular illuminating beam (15b) toward the right eye (13); and second optical combining means (6, 28) able to superpose the left ocular stimulating beam (14a) and the left monocular illuminating beam (15a), and second optical means for directing the left ocular stimulating beam (14a) and the left monocular illuminating beam (15a) toward the left eye (12).

2. The binocular multiplexing device (100) as claimed in claim 1, in which said first optical splitting means (4, 25) comprise a beam-splitting plate or a beam-splitting cube.

3. The binocular multiplexing device (100) as claimed in claim 2, comprising an electronic processing unit suitable for receiving a signal representative of the switching state of said optical switching means (5, 24, 43, 44, 45) and to receive, in sequence, a first measurement representative of said right ocular measuring beam (55b) and a second measurement representative of said left ocular measuring beam (55a), said electronic processing unit being able to combine said signal representative of the switching state and said first and second measurements in order to deliver a multiplexed binocular measurement of at least one vision parameter.

4. The binocular multiplexing device (100) as claimed in claim 1, in which said optical switching means (5, 24, 43, 44, 45) comprise a dichroic plate, an orientable mirror (24), a retractable mirror, an electro-optical modulator, an acousto-optical modulator and/or polarization-selecting means (43, 44, 45, 46).

5. The binocular multiplexing device (100) as claimed in claim 1, in which said second optical splitting means are merged with said optical switching means, or in which said second optical splitting means comprise a beam-splitting plate or a beam-splitting cube.

6. The binocular multiplexing device (100) as claimed in claim 1, in which said first optical combining means comprise a dichroic plate (7, 29) able to superpose a right ocular stimulating beam (14b) in the visible domain and a right monocular illuminating beam (15b) in the infrared domain, and/or said second optical combining means comprise a dichroic plate (6, 28) able to superpose a left ocular stimulating beam (14a) in the visible domain and a left monocular illuminating beam (15a) in the infrared domain, respectively.

7. The binocular multiplexing device (100) as claimed in claim 1, furthermore comprising an optical port (22, 35) for coupling to an ophthalmological instrument (110) having a single measuring channel, said optical coupling port (22, 35) being able to receive a stimulating image beam (14) issued from a stimulus test pattern, and a single illuminating beam (15), and to transmit a single measuring beam (55), and mechanical and/or opto-mechanical means for aligning said ophthalmological instrument (110) having a single measuring channel and said binocular multiplexing device (100), said mechanical and/or opto-mechanical aligning means comprising an alignment test pattern (48, 50) able to emit an optical aligning beam, and optical means (47, 51, 52) able to superpose said aligning optical beam (60) and said single measuring beam (55) in the optical coupling port (22, 35).

8. An ophthalmological instrument (120) for multiplexed binocular measurement of at least one vision parameter of a subject, said ophthalmological instrument comprising a binocular multiplexing device (100) according to claim 7, and:

ophthalmological means (2) for measuring at least one vision parameter of a subject, said ophthalmological measuring means being able to generate a single illuminating beam (15) and to receive and analyze a single measuring beam (55) generated by reflection and/or refraction of said single illuminating beam from an eye (12, 13) of the subject, said single illuminating beam (15) and said single measuring beam (55) following reciprocal optical paths between said ophthalmological measuring means (2) and the eye (12, 13) of the subject.

9. The binocular multiplexing device (100) as claimed in claim 1, comprising a right exit pupil (37), a left exit pupil (36) and imaging optical means (20, 21, 23, 32, 33, 34), said right exit pupil (37) being able to receive said right monocular illuminating beam (15b) and said right ocular measuring beam (55b), and said left exit pupil (36) being able to receive said left monocular illuminating beam (15a) and said left ocular measuring beam (55a), respectively, and said imaging optical means (18, 19, 20, 21, 23, 32, 33, 34) being able to form the image of an exit pupil (22, 35) of said ophthalmological instrument (100) having a single measuring channel on said right exit pupil (37) and/or said left exit pupil (36).

10. The binocular multiplexing device (100) as claimed in claim 9, comprising secondary illuminating means (160, 161) able to emit a secondary illuminating beam (170, 171) in the direction of the cornea of each eye (12, 13) so as to generate a right ocular measuring beam (55b) and a left ocular measuring beam (55a), respectively, in order to provide an analysis of the cornea by keratometry and/or corneal topography.

11. The binocular multiplexing device (100) as claimed in claim 9, comprising:
- a right optical system (9, 11, 21) placed between the first optical combining means (7, 29) and the right eye (13) of the subject;
- a left optical system (8, 10, 20) placed between the second optical combining means (6, 28) and the left eye (12) of the subject; and
- means (30, 31, 32, 33) for aligning said right optical system (9, 11, 21, 33) and said left optical system (8, 10, 20, 32) so as to adjust the pupillary distance depending on the prismatic convergence of the subject.

12. The binocular multiplexing device (100) as claimed in claim 1, furthermore comprising an optical system (3) placed on the optical path of the stimulating image beam (14), said optical system (3) being able to correct an average sphere error of the two eyes (12, 13).

13. The binocular multiplexing device (100) as claimed in claim 1, furthermore comprising a first optical system (18, 26) placed on the optical path of the right ocular stimulating beam (14b) and a second optical system (19, 27) placed on the optical path of the left ocular stimulating beam (14a), said first optical system (18, 26) and said second optical system (19, 27) being able to correct a sphere and/or cylinder error of the right eye (13) and of the left eye (12) of the subject, respectively.

14. The binocular multiplexing device (100) as claimed in claim 1, comprising:
- a right optical system (9, 11, 21) placed between the first optical combining means (7, 29) and the right eye (13) of the subject;
- a left optical system (8, 10, 20) placed between the second optical combining means (6, 28) and the left eye (12) of the subject; and
- means (30, 31, 32, 33) for aligning said right optical system (9, 11, 21, 33) and said left optical system (8, 10, 20, 32) so as to adjust the pupillary distance depending on the prismatic convergence of the subject.

15. The binocular multiplexing device as claimed in claim 1, in which, the optical paths of the stimulating image beam (14), of the single illuminating beam (15) and of the single measuring beam (55) being merged, said binocular multiplexing device comprises:
- third optical splitting means (42) able to receive and to spatially split said stimulating image beam (14) and said single illuminating beam (15), said third optical splitting means (42) being able to receive said single measuring beam (55) along an optical path that is the reverse of that of said single illuminating beam (15).

16. The binocular multiplexing device (100) as claimed in claim 1, in which said third optical splitting means comprise a beam-splitting plate (42) able to split a stimulating image beam (14) in the visible domain and an illuminating beam (15) in the infrared domain.

17. The binocular multiplexing device (100) as claimed in claim 1, comprising an electronic processing unit suitable for receiving a signal representative of the switching state of said optical switching means (5, 24, 43, 44, 45) and to receive, in sequence, a first measurement representative of said right ocular measuring beam (55b) and a second measurement representative of said left ocular measuring beam (55a), said electronic processing unit being able to combine said signal representative of the switching state and said first and second measurements in order to deliver a multiplexed binocular measurement of at least one vision parameter.

18. An ophthalmological instrument (120) for multiplexed binocular measurement of at least one vision parameter of a subject, said ophthalmological instrument comprising a binocular multiplexing device (100) according to claim 1, and:
- ophthalmological means (2) for measuring at least one vision parameter of a subject, said ophthalmological measuring means being able to generate a single illuminating beam (15) and to receive and analyze a single measuring beam (55) generated by reflection and/or refraction of said single illuminating beam from an eye (12, 13) of the subject, said single illuminating beam (15) and said single measuring beam (55) following reciprocal optical paths between said ophthalmological measuring means (2) and the eye (12, 13) of the subject.

19. A method for determining at least one binocular vision parameter of a subject, said method comprising the following steps:
a) delivering a stimulating image beam (14) for a proximity value P;
b) splitting the stimulating image beam (14) into a right ocular stimulating beam (14b) and a left ocular stimulating beam (14a) so as to stimulate accommodation by the right eye (13) and by the left eye (12) of the subject simultaneously;
c) generating a right monocular illuminating beam (15b) and/or a left monocular illuminating beam (15a);
d) optically superposing said right ocular stimulating beam (14b) and said right monocular illuminating beam (15b) in a right optical channel (17) and/or optically superposing said left ocular stimulating beam (14a) and said left monocular illuminating beam (15a) in a left optical channel (16), respectively;
e) collecting the right monocular measuring beam (55b) or the left monocular measuring beam (55a) along an optical path that is the inverse of that of the right monocular illuminating beam (15b) and of the left monocular illuminating beam (15a), respectively;
f) analyzing the right monocular measuring beam (55b) or the left monocular measuring beam (55a) so as to determine at least one right monocular vision parameter or left monocular vision parameter, respectively; and
g) repeating steps c) to f) after switching of the monocular measuring beam (55a, 55b), so as to determine at least one binocular vision parameter of a subject using the same ocular stimulations for the right eye (13) and left eye (12) of the subject.

20. A method for determining at least one objective binocular vision parameter of a subject, comprising carrying out the steps of the method as claimed in claim 19 for a first proximity value P1, then carrying out the steps of the method for at least one other proximity value Pn.

21. The method as claimed in claim 19, in which step c) of generating a right monocular illuminating beam (15b) and/or a left monocular illuminating beam (15a) is carried out by dividing or switching a single illuminating beam (15).

\* \* \* \* \*